(12) United States Patent
Shoji

(10) Patent No.: US 7,223,880 B2
(45) Date of Patent: May 29, 2007

(54) PHOSPHORUS-CONTAINING ORGANOSILICON COMPOUND, A METHOD FOR PRODUCING THE SAME, AND A RESIN COMPOSITION OR A COATING COMPOSITION CONTAINING THE SAME

(75) Inventor: Hiroaki Shoji, Tokyo (JP)

(73) Assignee: Nippon Unicar Company Limited, Tokyo (JP)

( * ) Notice: Subject to any disclaimer, the term of this patent is extended or adjusted under 35 U.S.C. 154(b) by 477 days.

(21) Appl. No.: 10/502,799

(22) PCT Filed: Dec. 8, 2003

(86) PCT No.: PCT/JP03/15676

§ 371 (c)(1),
(2), (4) Date: Aug. 5, 2004

(87) PCT Pub. No.: WO2004/052897

PCT Pub. Date: Jun. 24, 2004

(65) Prior Publication Data

US 2005/0154223 A1 Jul. 14, 2005

(30) Foreign Application Priority Data

Dec. 10, 2002 (JP) .............................. 2002-358269

(51) Int. Cl.
*C07F 9/02* (2006.01)
(52) U.S. Cl. ...................................... 556/405
(58) Field of Classification Search ................ 556/405
See application file for complete search history.

(56) References Cited

U.S. PATENT DOCUMENTS 5,627,169 A    5/1997    Miledi et al.

FOREIGN PATENT DOCUMENTS

| EP | 65374 A1 | 11/1982 |
|----|----------|---------|
| JP | 49-45397 | 12/1974 |
| JP | 50-17979 | 6/1975 |
| JP | 63-43964 | 2/1988 |
| JP | 3-44080 | 7/1991 |
| JP | 2000-212419 | 8/2000 |
| JP | 2001-247582 | 9/2001 |

*Primary Examiner*—Samuel Barts
(74) *Attorney, Agent, or Firm*—Armstrong, Kratz, Quintos, Hanson & Brooks, LLP

(57) ABSTRACT

The present invention provides a novel phosphorus-containing organosilicon compound furnished with performance of an oxaphosphorin compound, a method for producing therefore and a resin composition containing the same, particularly a polyester or polycarbonate resin composition and a coating composition containing the same, characterized by that said phosphorus-containing organosilicon compound has in the molecule a phosphorus-containing group (an X group) bonded to a silicon atom and represented by the following chemical formula (1)

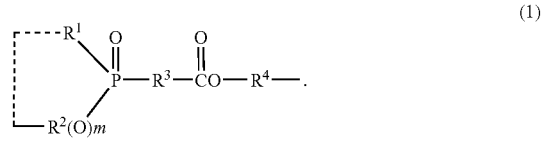

(1)

16 Claims, No Drawings

PHOSPHORUS-CONTAINING ORGANOSILICON COMPOUND, A METHOD FOR PRODUCING THE SAME, AND A RESIN COMPOSITION OR A COATING COMPOSITION CONTAINING THE SAME

BACKGROUND OF THE INVENTION

1. Field of the Invention

The present invention relates to a novel phosphorus-containing organosilicon compound, a method for producing the same and a resin composition or a coating composition containing the same. In more detail, the present invention relates to a phosphorus-containing organosilicon compound, that has a phosphorus-containing group bonded to a silicon atom in the molecule and is furnished with performance of an oxaphosphorin compound, a method for producing the same and a resin composition or a coating composition containing the same.

2. Description of the Prior Art

An oxaphosphorin compound is useful as a flame retardant for a resin and a phosphorus-containing dicarboxylic acid derived therefrom is useful as a plasticizer for polymers. A phosphorus-containing dicarboxylic acid derived from an oxaphosphorin compound can be suitably used for manufacturing of a resin composition with flame retardance, for instance, a flame retardant polyester can be manufactured by using a phosphorus-containing dicarboxylic acid as a comonomer.

In addition, a phosphorus-containing dicarboxylic acid and ester derivatives thereof are known to possess flame resistance, flame retardance and antibiotic action (particularly, antibiotic durability) as well as to be a component of a polyester composition that can form molded parts such as fibers and films with sufficient consideration on safety (for example, see JP-A-2000-212419 (on claims and the like).

Further, various kinds of silicon compounds are widely used to reinforce bonds among inorganic materials such as metals and inorganic fillers and organic resins (coupling function), or to coat surface of inorganic or organic materials and to be loaded or copolymerized into resins as modifiers to improve surface properties thereof and resins themselves (for example, to enhance water repellency, mold release performance, lubricating performance, heat resistance, flexibility and impact resistance).

Still further, phosphorylated polyorganosiloxane is also known to have flame retardant effect and to function as a flame retardant (for example, see JP-A-2001-247582 (on claims and the like).

However, there have not been any proposals on compounds by stable bonds between an oxaphosphor in compound and a silicon compound, having superior performance of both compounds.

Therefore, a silicon compound furnished with performance of an oxaphosphorin compound and can be available industrially has been required. There have also been needs for resin compositions or coating compositions having improved performance, which are loaded with the above compounds.

SUMMARY OF THE INVENTION

An object of the present invention is to provide a novel phosphorus-containing organosilicon compound, furnished with performance of an oxaphosphorin compound, a method for producing the same and a resin composition containing the same, particularly a polyester or polycarbonate resin composition, or a coating composition containing the same.

After intensive study to solve the above-described problems, the present inventors have found that a novel phosphorus-containing organosilicon compound, furnished with performance of an oxaphosphorin compound can be obtained by selecting 3,4,5,6-dibenzo-1,2-oxaphosphane-2-oxide (another name: 9,10-dihydro-9-oxa-10-phosphaphenanthrene-10-oxide) as an oxaphosphorin compound and reaction of the above compound with a silicon compound having an unsaturated ester group. These knowledge and further study have brought about the present invention.

The first aspect of the invention provides a phosphorus-containing organosilicon compound, characterized by having in the molecule a phosphorus-containing group (an X group) bonded to a silicon atom and represented by the following chemical formula (1).

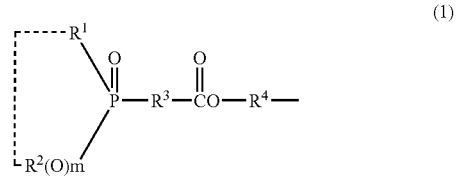

(wherein $R^1$ and $R^2$ may be the same or different, and each represents a linear or branched alkyl group having 1 to 8 carbon atoms, an alicyclic group having 5 to 6 carbon atoms in the ring, an unsubstituted or substituted aryl group having 6 to 10 carbon atoms or a group forming a 5 to 8-membered ring with a phosphorus atom; m is 0 or 1; and $R^3$ and $R^4$ each independently represents a substituted or unsubstituted bivalent hydrocarbon group).

The second aspect of the invention provides a phosphorus-containing organosilicon compound, characterized by being represented by the following chemical formula (2):

[wherein X is a phosphorus-containing group represented by the chemical formula (1):

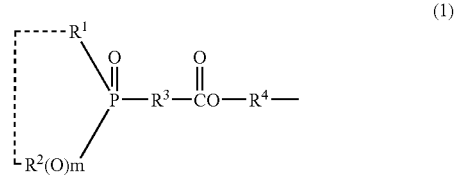

(wherein $R^1$ and $R^2$ may be the same or different, and each represents a linear or branched alkyl group having 1 to 8 carbon atoms, an alicyclic group having 5 to 6 carbon atoms in the ring, an unsubstituted or substituted aryl group having 6 to 10 carbon atoms, or a group forming a 5 to 8-membered ring with a phosphorus atom; m is 0 or 1; $R^3$ and $R^4$ each independently represents a substituted or unsubstituted bivalent hydrocarbon group); $R^5$ represents the same or different organic groups selected from an alkyl group, an aryl group, an aralkyl group, and a fluorine-substituted alkyl or alkoxy group each having 1 to 30 carbon atoms; and a and b are numbers in the range of $0.001 \leq a \leq 1.5$ and $0 \leq b \leq 3.0$, respectively].

The third aspect of the invention provides a phosphorus-containing organosilicon compound which is the same as that of the second aspect, wherein the chemical formula (2) is represented by the following chemical formula (3).

$$R^5{}_3SiO\text{—}(R^5{}_2SiO)x(R^5X\ SiO)y\text{-}SiR^5{}_3 \qquad (3)$$

(wherein $R^5$ and X are each the same as the above; x is an integer of 0 or not less than 1; and y is an integer of not less than 1).

The fourth aspect of the invention provides a phosphorus-containing organosilicon compound or a condensate thereof, characterized by being represented by the following chemical formula (4):

$$XSiR^6{}_c(OR^7)_{(3-c)} \qquad (4)$$

[wherein X is a phosphorus-containing group represented by the chemical formula (1):

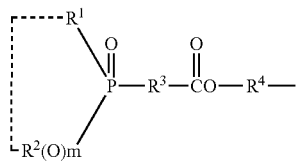

(wherein, $R^1$ and $R^2$ may be the same or different, and each represents a linear or branched alkyl group having 1 to 8 carbon atoms, an alicyclic group having 5 to 6 carbon atoms in the ring, an unsubstituted or substituted aryl group having 6 to 10 carbon atoms, or a group forming a5 to 8-membered ring with a phosphorus atom; m is 0 or 1; and $R^3$ and $R^4$ each independently represents a substituted or unsubstituted bivalent hydrocarbon group); $R^6$ is the same or different organic groups selected from an alkyl group, an aryl group, an aralkyl group, and a fluorine-substituted alkyl group each having 1 to 30 carbon atoms; $R^7$ represents the same or different organic groups selected from an alkyl group, an aryl group, an aralkyl group, and a fluorine-substituted alkyl group each having 1 to 30 carbon atoms; and c is 0 or 1], is provided.

The fifth aspect of the invention provides a phosphorus-containing organosilicon compound, characterized by being represented by the following chemical formula (5):

$$XSiR^5{}_c(OSiR^8{}_3)_{(3-c)} \qquad (5)$$

[wherein X is a phosphorus-containing group represented by the chemical formula (1):

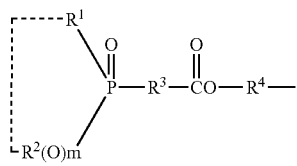

(wherein $R^1$ and $R^2$ may be the same or different, and each represents a linear or branched alkyl group having 1 to 8 carbon atoms, an alicyclic group having 5 to 6 carbon atoms in the ring, an unsubstituted or substituted aryl group having 6 to 10 carbon atoms, or a group forming a 5 to 8-membered ring with a phosphorus atom; m is 0 or 1; and $R^3$ and $R^4$ each independently represents a substituted or unsubstituted bivalent hydrocarbon group); $R^5$ is the same or different organic groups selected from an alkyl group, an aryl group, an aralkyl group, and a fluorine-substituted alkyl or alkoxy group each having 1 to 30 carbon atoms; $R^8$ represents the same or different organic groups selected from an alkyl group, an aryl group, an aralkyl group, and a fluorine-substituted alkyl or alkoxy group each having 1 to 30 carbon atoms; and c is 0 or 1].

The sixth aspect of the invention provides a phosphorus-containing organosilicon compound or a condensate thereof which is the same as that of the any one of the above first to 5th aspects, characterized in that a phosphorus-containing group (an X group) is represented by the following chemical formula (6):

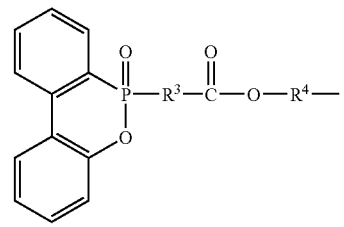

(wherein $R^3$ and $R^4$ each independently represents a substituted or unsubstituted bivalent hydrocarbon group).

The seventh aspect of the invention provides a method for producing a phosphorus-containing organosilicon compound or a condensate thereof which is the same as that of the any one of the above first to 6th aspects, characterized by being obtained by reaction of a compound represented by the following chemical formula (7):

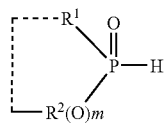

(wherein $R^1$ and $R^2$ may be the same or different, and each represents a linear or branched alkyl group having 1 to 8 carbon atoms, an alicyclic group having 5 to 6 carbon atoms in the ring, an unsubstituted or substituted aryl group having 6 to 10 carbon atoms, or a group forming a 5 to 8-membered ring with a phosphorus atom; and m is 0 or 1) and a silicon compound having an unsaturated ester group bonded to a silicon atom in the molecule and represented by the following chemical formula (8):

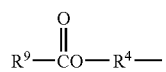

(wherein $R^4$ represents a substituted or unsubstituted bivalent hydrocarbon group; and $R^9$ represents a substituted or unsubstituted unsaturated hydrocarbon group).

The eighth aspect of the invention provides a method for producing a phosphorus-containing organosilicon compound or a condensate thereof which is the same as that of the 4th aspect, characterized by being obtained by reaction of a compound represented by the following chemical formula (7):

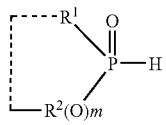
(7)

(wherein $R^1$ and $R^2$ may be the same or different, and each represents a linear or branched alkyl group having 1 to 8 carbon atoms, an alicyclic group having 5 to 6 carbon atoms in the ring, an unsubstituted or substituted aryl group having 6 to 10 carbon atoms or a group forming a 5 to 8-membered ring with a phosphorus atom; and m is 0 or 1), and a silicon compound represented by the following chemical formula (9):

[wherein Y is an unsaturated ester group represented by the chemical formula (8):

(wherein $R^4$ represents a substituted or unsubstituted bivalent hydrocarbon group; $R^9$ represents a substituted or unsubstituted unsaturated hydrocarbon group); $R^6$ represents the same or different organic groups selected from an alkyl group, an aryl group, an aralkyl group and a fluorine-substituted alkyl group each having 1 to 30 carbon atoms; $R^7$ represents the same or different organic groups selected from an alkyl group, an aryl group, an aralkyl group and a fluorine-substituted alkyl group each having 1 to 30 carbon atoms; and c is 0 or 1].

The ninth aspect of the invention provides a method for producing a phosphorus-containing organosilicon compound which is the same as that of the any one of the 1st to 3rd, 5th and 6th aspects, characterized by being obtained by using a phosphorus-containing organosilicon compound or a condensate thereof of the above 4th aspect as an intermediate.

The tenth aspect of the invention provides a resin composition, characterized by containing a phosphorus-containing organosilicon compound or a condensate thereof which is the same as that of the any one of the 1st to 6th aspects.

The eleventh aspect of the invention provides a resin composition which is the same as that of the 10th aspects, characterized by being a polyester or polycarbonate resin composition.

The twelfth aspect of the invention, a coating composition, characterized by containing a phosphorus-containing organosilicon compound or a condensate which is the same as that of the any one of the 1st to 6th aspects.

As described above, the present invention relates to a phosphorus-containing organosilicon compound or the like, characterized by having in the molecule a phosphorus-containing group (an X group) bonded to a silicon atom and represented by the above chemical formula (1), and a preferable embodiment of the invention includes following items.

(I) A method for producing a phosphorus-containing organosilicon compound and a condensate thereof in the above 7th or 8th aspects, characterized by performing a reaction, in the presence of a solvent, between a compound represented by the chemical formula (7) and a silicon compound containing an unsaturated ester group of represented by the chemical formula (8) or (9).

(II) A method for producing a phosphorus-containing organosilicon compound and a condensate thereof in the above 7th or 8th aspects, characterized in that a compound represented by the chemical formula (7) is 3,4,5,6-dibenzo-1,2-oxa phosphane-2-oxide (another name:9,10-dihydro-9-oxa-10-phosphaphenanthrene-10-oxide).

(III) A resin composition in the above 10th aspect, characterized by further containing at least one kind of additives, selected from flame retardants, inorganic particles, organic particles, fibers, anti-dripping agents, dyes, pigments, plasticizers, crosslinking agents, ultraviolet absorbers, light stabilizers, antioxidants, antirust agents, antibiotics, fungicides or anti-algae agents.

(IV) A coating composition in the above 12th aspect, characterized by further containing at least one kind of additives, selected from resins, dyes, pigments, antistatic agents, crosslinking agents, antifogging agents, viscosity modifier, dispersing agents, surfactants, nucleating agents, lubricants, ultraviolet absorbers, light stabilizers, antioxidants, antirust agents, antibiotics, fungicides or anti-algae agents.

DETAILED DESCRIPTION OF THE INVENTION

A phosphorus-containing organosilicon compound of the present invention, a method for producing the same and a resin composition containing the same will be explained in detail bellow.

1. A Phosphorus-containing Organosilicon Compound

A phosphorus-containing organosilicon compound of the present invention is one characterized by having in the molecule a phosphorus containing group (an X group) bonded to a silicon atom and represented by the following chemical formula (1).

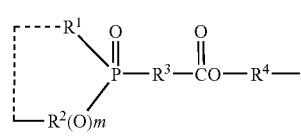
(1)

wherein $R^1$ and $R^2$ may be the same or different and each represents a linear or branched alkyl group having 1 to 8 carbon atoms, an alicyclic group having 5 to 6 carbon atoms in the ring, a substituted or unsubstituted aryl group having 6 to 10 carbon atoms, or $R^1$ and $R^2$ may form a 5 to 8 membered ring together with a phosphorus atom; m represents 0 or 1; $R^3$ and $R^4$ each independently represents a substituted or unsubstituted bivalent hydrocarbon group.

In the present invention it is useful to use a phosphorus-containing organosilicon compound wherein $R^1$ and $R^2$ preferably forms a 6 to 7 membered ring together with a phosphorus atom in the above-described chemical formula (1), and when an oxygen atom is present (m=1) it is counted as a ring member.

In a more preferable compound, $R^1$ and $R^2$ may be the same or different and each represents a linear or branched alkyl group having 1 to 4 carbon atoms, a cyclopentyl group or a cyclohexyl group, an aryl group substituted with not less than one halogen, alkyl group, alkoxy group or aryl group, or $R^1$ and $R^2$ may form a substituted or unsubstituted oxa phosphorin ring together with a phosphorus atom.

In a further preferable compound, $R^1$ and $R^2$ may be the same or different and each represents a phenyl group or a phenyl group substituted with one or two of alkyl groups or alkoxy groups having 1 to 4 carbon atoms; and m=0.

Most preferably, a phosphorus containing group (an X group) represented by the chemical formula (1) is a group containing an oxa phosphorin ring and shown by the chemical formula (6'):

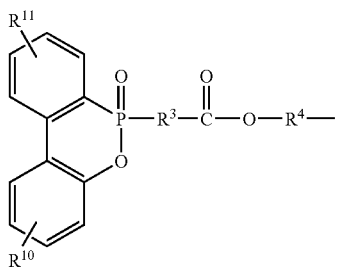

(6')

(wherein $R^3$ and $R^4$ each independently represents a substituted or unsubstituted bivalent hydrocarbon group; and $R^{10}$ and $R^{11}$ may be the same or different each other and each represents a hydrogen atom, a halogen atom, an alkyl group having 1 to 4 carbon atoms or an alkoxy group having 1 to 4 carbon atoms.) In the chemical formula (6'), $R^{10}$ and $R^{11}$ each is preferably a hydrogen atom and this case responds to the above-described chemical formula (6) relevant to the above sixth aspect of the present invention.

Furthermore, in a phosphorus-containing organosilicon compound of the present invention, $R^3$ and $R^4$ in the above-described chemical formula (1) each independently represents a substituted or unsubstituted bivalent hydrocarbon group, each preferably a substituted or unsubstituted bivalent hydrocarbon group having 1 to 8 carbon atoms and each more preferably a substituted or unsubstituted bivalent hydrocarbon group having 1 to 4 carbon atoms.

A phosphorus-containing organosilicon compound of the present invention is also one characterized by being represented by the following chemical formula (2):

$$X_a R^5{}_b SiO_{(4-a-b)/2} \quad (2)$$

wherein X represents a phosphorus-containing group shown by the above-described chemical formula (1); $R^5$s represent the same or different organic groups selected from an alkyl group, an aryl group, an aralkyl group and an alkyl group or an alkoxy group substituted with a fluorine atom, having 1 to 30 carbon atoms; preferably the same or different organic groups selected from an alkyl group, an aryl group, an aralkyl group and an alkyl group or an alkoxy group substituted with a fluorine atom, having 1 to 8 carbon atoms; and more preferably the same or different organic groups selected from an alkyl group, an aryl group, an aralkyl group and an alkyl group or an alkoxy group substituted with a fluorine atom, having 1 to 6 carbon atoms; and a and b represents numbers within the range of $0.001 \leq a \leq 1.5$ and $0 \leq b \leq 3.0$, respectively.

The expression method in the above-described chemical formula (2) is a unique one to those skilled in the art on polysiloxane, that represents number of each element or a group based on one silicon atom. For example, polysiloxane represented by $R^5{}_3SiO-(R^5{}_2SiO)_{100}(R^5XSiO)_{10}-SiR^5{}_3$ can be expressed as $X_{10}R^5{}_{216}Si_{112}O_{111} = X_{10/112} R^5{}_{216/112}SiO_{111/112}$, that is, $X_{0.09}R^5{}_{1.93}SiO_{0.99}$.

Therefore, a phosphorus-containing organosilicon compound of the present invention represented by the chemical formula (2) can also be expressed by the following chemical formula (3):

$$R^5{}_3SiO-(R^5{}_2SiO)x(R^5XSiO)y-SiR^5{}_3 \quad (3)$$

(wherein $R^5$ and X represent the same as described above; x is an integer of 0 or not smaller than 1; and y is an integer not smaller than 1).

A phosphorus-containing organosilicon compound of the present invention is one characterized by being expressed by the following chemical formula (4):

$$XSiR^6{}_c(OR^7)_{(3-c)} \quad (4)$$

and a condensed compound of a phosphorus-containing organosilicon compound expressed by the following chemical formula (4) is also included in the present invention.

In the above-described chemical formula (4), X represents a phosphorus containing group shown by the above-described chemical formula (1); $R^6$ represents an organic group selected from an alkyl group, an aryl group, an aralkyl group or an alkyl group substituted with a fluorine atom, having 1 to 30 carbon atoms, preferably the same or a different organic group selected from an alkyl group, an aryl group, an aralkyl group or an alkyl group substituted with a fluorine atom, having 1 to 8 carbon atoms and more preferably the same or a different organic group selected from an alkyl group, an aryl group, an aralkyl group or an alkyl group substituted with a fluorine atom, having 1 to 6 carbon atoms; and $R^7$s represent the same or a different organic groups selected from an alkyl group, an aryl group, an aralkyl group or an alkyl group substituted with a fluorine atom, having 1 to 30 carbon atoms, preferably the same or different organic groups selected from an alkyl group, an aryl group, an aralkyl group or an alkyl group substituted with a fluorine atom, having 1 to 8 carbon atoms and more preferably the same or a different organic group selected from an alkyl group, an aryl group or an alkyl group substituted with a fluorine atom, having 1 to 4 carbon atoms; and c represents 0 or 1.

Furthermore, a phosphorus-containing organosilicon compound of the present invention is one characterized by being expressed by the following chemical formula (5):

$$XSiR^5{}_c(OSiR^8{}_3)_{(3-c)} \quad (5)$$

wherein X represents a phosphorus containing group shown by the above-described chemical formula (1); $R^8$s represents the same or different organic groups selected from an alkyl group, an aryl group, an aralkyl group and an alkyl group or an alkoxy group substituted with a fluorine atom, having 1 to 30 carbon atoms; preferably the same or different organic groups selected from an alkyl group, an aryl group, an aralkyl group and an alkyl group or an alkoxy group substituted with a fluorine atom having 1 to 8 carbon atoms; and more preferably the same or different organic groups selected from an alkyl group, an aryl group and an alkyl group or an alkoxy group substituted with a fluorine atom, having 1 to 6 carbon atoms; and c is 0 or 1.

2. A Method for Producing a Phosphorus-containing Organosilicon Compound

In a method for producing a phosphorus-containing organosilicon compound of the present invention, in particular, a compound expressed by the following chemical formula (7):

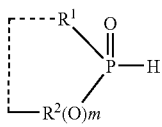

(wherein $R^1$ and $R^2$ may be the same or different and each represents a linear or branched alkyl group having 1 to 8 carbon atoms, an alicyclic group having 5 to 6 carbon atoms in the ring, a substituted or unsubstituted aryl group having 6 to 10 carbon atoms, or $R^1$ and $R^2$ may form a 5 to 8 membered ring together with a phosphorus atom; m represents 0 or 1) is reacted with a silicon compound containing an unsaturated ester group bonded to the silicon atom in the molecule and expressed by the following chemical formula (8):

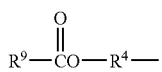

(wherein $R^4$ represents a substituted or unsubstituted bivalent hydrocarbon group; and $R^9$ represents a substituted or unsubstituted unsaturated hydrocarbon group).

Usually the former compound is used in stoichiometric ratio to an unsaturated ester group of the latter compound or one of the two compounds is used in excess amount.

A compound represented by the chemical formula (7) can be manufactured by known methods, for example, methods disclosed in JP-B2-49-45397, JP-B2-50-17979 or JP-B2-3-44080. Typically, "SANKO-HCA" or "SANKO-EPO-CLEAN" sold from Sanko Co. Ltd., chemical name being 3,4,5,6-dibenzo-1,2-oxaphosphane-2-oxide (in another name: 9,10-dihydro-9-oxa-10-phosphaphenanthrene-10-oxide) is suitably used.

In the above-described chemical formula (8), $R^9$ represents, as shown above, a substituted or unsubstituted unsaturated hydrocarbon group, preferably an unsubstituted unsaturated hydrocarbon group having 1 to 8 carbon atoms, more preferably an unsubstituted unsaturated hydrocarbon group having 1 to 4 carbon atoms.

Reaction between a compound by the chemical formula (7) and a silicon compound having an unsaturated ester group represented by the chemical formula (8) may be performed in a non-solvent system, however, a solvent may be used to enhance solubility.

A solvent includes alcohols such as methanol, ethanol and isopropanol; esters such as methyl acetate and ethyl acetate; saturated aliphatic carboxylic acids such as acetic acid and propionic acid; ethers such as tetrahydrofran and dimethyl ether; amides, amines and sulfoxides and not specifically limited, however, alcohols and saturated aliphatic carboxylic acids are preferable.

Reaction temperature is not specifically limited, however, generally 100 to 200° C., preferably 115 to 160° C. In the reaction at such temperature range or at lower temperature, pressurization may be adopted.

In a method for producing a phosphorus-containing organosilicon compound expressed by the above-described chemical formula (4), relevant to the above 4th aspect, a compound represented by the above-described chemical formula (7) and a silicon compound represented by the following chemical formula (9):

$$YSiR^6_c(OR^7)_{(3-c)} \qquad (9)$$

are reacted.

In the chemical formula (9), Y represents an unsaturated ester group represented by the above-described chemical formula (8); $R^6$ represents an organic group selected from an alkyl group, an aryl group, an aralkyl group and an alkyl group substituted with a fluorine atom, having 1 to 30 carbon atoms; $R^7$s represent the same or a different organic groups selected from an alkyl group, an aryl group, an aralkyl group and an alkyl group substituted with a fluorine atom, having 1 to 30 carbon atoms; and c is 0 or 1.

Furthermore, a phosphorus-containing organosilicon compound in accordance with the present invention can also be obtained by using a phosphorus-containing organosilicon compound relevant to the above 4th aspect and represented by the above-described chemical formula (4) or a condensed compound thereof as an intermediate.

Typically, said phosphorus-containing organosilicon compound can be obtained by reaction of a phosphorus-containing organosilicon compound represented by the chemical formula (4) or a condensed compound thereof and a silicon compound (a siloxane compound) such as 1,3,5,7-octamethyltetracyclosiloxane or hexamethyldisiloxane in the presence of an acidic catalyst or in the presence of a carboxylic acid and a strong acid.

3. A Resin Composition

A resin used in a resin composition containing a phosphorus-containing organosilicon compound of the present invention includes a urea resin, a melamine resin, a polyamide resin, a polyimide resin, a polyester resin, an alkyd resin, an epoxy resin, a furan resin, a polyurethane resin, an isocyanate resin, a silicone resin, a silicate resin, a phenol resin, a resorcinol resin, a polycarbonate resin, a polyethylene resin, a polypropylene resin, a polybutadiene resin, a polyisoprene resin, a polysulfide resin, a polystyrene resin, a nitrile resin, a polyvinyl alcohol resin, an acryl resin, a polyvinyl acetate resin and a polyvinyl chloride resin and a composite resin among these resins and other high molecular weight or low molecular weight compounds, although specifically not limited to these. Preferable resins are a polyester resin and a polycarbonate resin and more preferable resin is a polycarbonate resin.

To a resin composition with a phosphorus-containing organosilicon compound of the present invention may be added, if necessary, with fire retardant materials (flame retardants) such as aluminum hydroxide, a silicon compound, an antimony compound, an organohalogen compound and a phosphorus compound; inorganic particles such as calcium carbonate, barium sulfate, calcium fluoride, talc, kaolin, silicon oxide, alumina, titanium oxide, zirconium oxide, iron oxide and an alumina/silica composite oxide; organic particles such as crosslinked polystyrene, crosslinked polymethacrylate esters and crosslinked polyacrylate esters; fibers such as carbon fiber and glass fiber; antidripping agents; inorganic and/or organic dyes; pigments; plasticizers; crosslinking agents; UV absorbers; light stabilizers; antioxidants; antirust agents; antibiotics; fungicides and anti-algae agents.

A resin composition with a phosphorus-containing organosilicon compound of the present invention can exert the effects as molded parts such as fibers and films, coating agents and other processing agents, because of having fire resistance, flame retardance and antibiotic performance (in particular, antibiotic durability), along with consideration on safety and in particular, improving surface performance or resin performance.

4. A Coating Composition

A phosphorus-containing organosilicon compound of the present invention can suitably be used as a coating agent to various substrates or a main component of a coating composition. In particular, it is useful to easily corrodible metal substrates such as a steel plate and a copper plate, due to having higher anti-rust effect than conventional coating agents. A coating composition containing the above-described phosphorus-containing organosilicon compound can be applied as it is, however it is preferable to use by dilution with a solvent due to providing uniform application. To said coating composition may be added, if necessary, additives used in conventional coating compositions such as resins, inorganic and/or organic dyes, pigments, antistatic agents, crosslinking agents, antifogging agents, viscosity improvers, dispersing agents, surfactants, nucleating agents, lubricants, UV absorbers, light stabilizers, antioxidants, antirust agents, antibiotics, fungicides and anti-algae agents.

EXAMPLES

The present invention will be explained in detail bellow using Examples and Comparative Examples, however, the present invention should by no means be limited to these Examples.

Example 1

To a 500 ml four-necked flask equipped with an agitator, an inlet for nitrogen gas introduction, a cooling tube and a thermometer, were charged 25.9 g (0.111 mol) of 3-methacryloxypropylmethyldimethoxysilane, 24.1 g (0.112 mol) of 3,4,5,6-dibenzo-1,2-oxa phosphane-2-oxide (in other name; 9,10-dihydro-9-oxa-10-phosphaphenanthrene-10-oxide) and 25.0 g of methanol, followed by heating up to 150° C. and reaction for 12 hours under stirring, while removing methanol by nitrogen gas flow to obtain 44.5 g of a product. Structure of thus obtained product was identified using GPC, IR absorption spectra, $^1$H-NMR and mass spectra to confirm that said product was a phosphorus-containing organosilicon compound (A) represented by the following chemical formula:

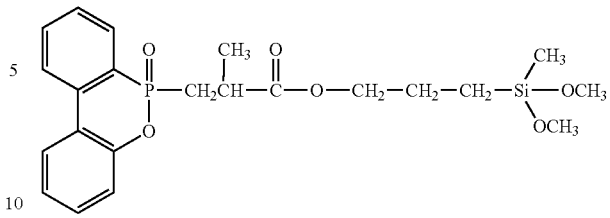

Example 2

To the similar equipment used in Example 1 were charged 164.1 g (0.66 mol) of 3-methacryloxytrimethoxysilane and 135.9 g (0.63 mol) of 3,4,5,6-dibenzo-1,2-oxaphosphophane-2-oxide, followed by flowing nitrogen gas, heating up to 150° C. and reaction for 14 hours, while stirring to obtain 282.0 g of a product. Structure of thus obtained product was identified using GPC, IR absorption spectra, $^1$H-NMR and mass spectra to confirm that said product was a phosphorus-containing organosilicon compound (B) represented by the following chemical formula (molecular weight of 464.5, viscosity of about 17,000 mm$^2$/s, refractive index of 1.567). By the way, a reaction mixture was slowly stirred (at 30 rpm) until 3,4,5,6-dibenzo-1,2-oxa phosphophane-2-oxide was dissolved (melting point: 110 to 120° C.).

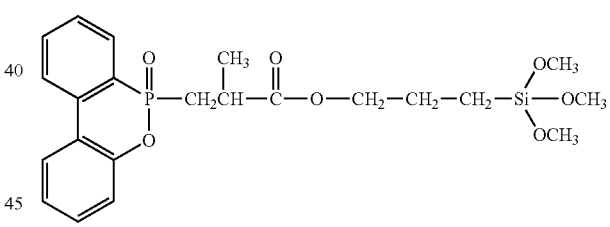

Example 3

To the similar equipment used in Example 1 were charged 149.2 g (0.33 mol) of the compound obtained in Example 1, 32.8 g (0.11 mol) of 1,1,3,3,5,5,7,7-octamethyltetracyclosiloxane, 18.0 g (0.11 mol) of hexamethyldisiloxane, 100 g of toluene, 5 g of sulfuric acid and 4.8 g of water, followed by stirring at room temperature for 10 hours, neutralization with sodium bicarbonate, washing with water and removing low volatile components by heating under reduced pressure to obtain a product. Structure of thus obtained product was identified using GPC, IR absorption spectra, $^1$H-NMR and mass spectra to confirm that said product was a phosphorus-containing organosilicon compound (C) represented by the following chemical formula:

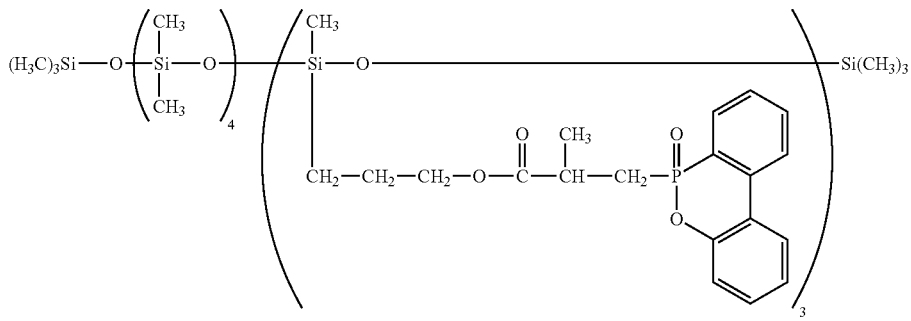

Example 4

To the similar equipment used in Example 1 were charged 198.6 g (0.47 mol) of 3-methacryloxypropyltris (trimethylsiloxy) silane, 101.4 g of 3,4,5,6-dibenzo-1,2-oxaphosphane-2-oxide and 50 g of propionic acid, followed by heating at 150° C. for 17 hours, while stirring and removing the solvent under reduced pressure to obtain 285.0 g of a product. Structure of thus obtained product was identified using GPC, IR absorption spectra, $^1$H-NMR and mass spectra to confirm that said product was a phosphorus-containing organosilicon compound (D) represented by the following chemical formula:

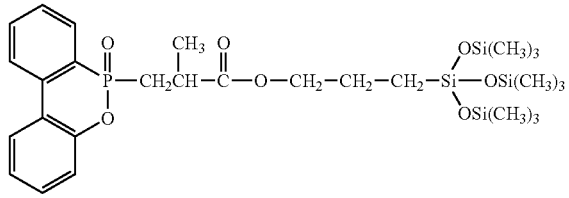

Example 5

To the similar equipment used in Example 1 were charged 95.6 g (0.206 mol) of the compound obtained in Example 2, 60.0 g (0.370 mol) of hexamethyldisiloxane, 44.4 g (0.74 mol) of acetic acid and 6 g of sulfuric acid, followed by reaction and the addition of 100 g of toluene, neutralization with sodium bicarbonate, washing with a saline solution and removing the solvent and low volatile components by heating under reduced pressure to obtain 82 g of a product. Structure of thus obtained product was identified using GPC, IR absorption spectra, $^1$H-NMR and mass spectra to confirm that said product was a phosphorus-containing organosilicon compound (D) (refractive index of 1.567), the same compound as obtained in Example 4.

Comparative Example 1

To the similar equipment used in Example 1 were charged 19.0 g (0.144 mol) of vinylmethyldimethoxysilane, 31.0 g (0.144 mol) of 3,4,5,6-dibenzo-1,2-oxaphosphane-2-oxide and 25.0 g of methanol, followed by reaction by heating up to 150° C. for 12 hours, while stirring and removing methanol by nitrogen gas flow. But no reaction was observed at all even after stirring for 12 hours and only raw materials were recovered.

Comparative Example 2

A reaction was performed under the same conditions as in Comparative Example 1, except that 10 g of a 5% methanol solution of sodium methoxide was added, however, no reaction was observed at all and only raw materials were recovered.

Comparative Example 3

A reaction was performed under the same conditions as in Example 2, except that 6 g of a 5% methanol solution of sodium methoxide was added. The same compound as obtained in Example 2 was obtained, however, ester moiety thereof was decomposed and yield was low.

Examples 6 to 26 and Comparative Examples 4 to 5

(Preparation and Evaluation of Resin Compositions)

A resin, a phosphorus-containing organosilicon compound obtained in each of Examples or Comparative Examples and an arbitrary component were mixed in accordance with formulations shown in the following Tables 1 to 3, followed by extrusion and pelletizing using 40 mm diameter single screw extruder (from Isuzu Machining Co., Ltd.) at cylinder temperature of 250° C.

Each pellet obtained was dried at 120° C. for 6 hours, followed by preparation of injection molded parts (test pieces for evaluation and measurement) using an injection molding machine ("J-50EP" from Japan Steel Works) at cylinder temperature of 270° C. and mold temperature of 80° C., which were subjected to evaluation of flame retardancy performance (initial state/after storage) and appearance, along with measurement of flexural modulus, Izod impact strength and heat distortion temperature. These results are shown in the following Tables 1 to 3.

Methods for evaluation and measurement of molded parts (resin compositions) are as follows:

Flame Retardancy Performance (Initial State)

Test pieces (5 pieces for each kind of a resin composition) with thickness of 1/16 inch were prepared in accordance with UL94 standard to be subjected to evaluation of flame retardancy performance based on the following criteria:

(V-0): Flammability period after removal of added flame to be within 10 seconds, total flammability period in 10 flame contacts to 5 test pieces to be within 50 seconds and no drop of spark which ignites absorbent cotton, from whole specimens.

(V-1): Flammability period after removal of added flame to be within 30 seconds, total flammability period in 10 flame contacts to 5 test pieces to be within 250 seconds and no drop of spark which ignites absorbent cotton, from whole specimens.

(V-2): Flammability period after removal of added flame to be within 30 seconds, total flammability period in 10 flame contacts to 5 test pieces to be within 250 seconds and spark drops which ignites absorbent cotton, from these specimens.

Flame Retardancy Performance (After Storage)

Test pieces (5 pieces for each kind of a resin composition) with thickness of 1/16 inch were prepared in accordance with UL94 standard, which were stored for 6 months in a thermostat chamber maintained at 26° C. and relative humidity of 65%, to be subjected to evaluation of flame retardancy performance similarly as the above-described tests.

Appearance

Molded parts were observed by naked eye and ranked as follows:

◎: very good
○: good
X: poor

Flexural Modulus

Flexural modulus was measured for test pieces prepared in accordance with ASTM D-790 standard.

Izod Impact Strength

Izod impact strength (at 23° C.) was measured in accordance with ASTM D-256 standard for 1/8 inch thick test pieces for notched impact strength prepared in accordance with ASTM D-256 standard.

Heat Distortion Temperature

Load distortion temperature was measured under 1820 kPa load for test pieces prepared in accordance with ASTM D-648 standard.

TABLE 1

| | Examples | | | | | | | |
|---|---|---|---|---|---|---|---|---|
| | 6 | 7 | 8 | 9 | 10 | 11 | 12 | 13 |
| resin type | PC | PC | PC | PC | PC | PC | PC | PC |
| a phosphorus-containing organosilicon compound (% by mass) *1 | | | | | | | | |
| A (Example 1) | 2 | — | — | — | — | 2 | — | — |
| B (Example 2) | — | 2 | — | — | — | — | 2 | — |
| C (Example 3) | — | — | 2 | — | — | — | — | — |
| D (Examples 4 and 5) | — | — | — | 2 | 10 | — | — | 2 |
| other additives (% by mass) *1 | | | | | | | | |
| an antidripping agent | — | — | — | — | — | — | 0.5 | — |
| talc | — | — | — | — | — | 7.5 | 15 | 15 |
| performance evaluation flame retardancy (rank) | | | | | | | | |
| initial state | V-0 | V-0 | V-0 | V-0 | V-0 | V-0 | V-0 | V-0 |
| after storage | V-0 | V-0 | V-0 | V-0 | V-0 | V-0 | V-0 | V-0 |
| appearance | ◎ | ◎ | ◎ | ◎ | ◎ | ◎ | ◎ | ◎ |
| flexural modulus ($10^3 \times$ Kg/cm$^2$) | 22 | 22 | 24 | 23 | 22 | 50 | 50 | 51 |
| impact strength (Kg · cm/cm) | 82 | 82 | 80 | 81 | 84 | 45 | 45 | 45 |
| heat distortion temperature (° C.) | 136 | 136 | 132 | 134 | 136 | 138 | 140 | 140 |

*1: based on total mass of a composition

TABLE 2

| | Examples | | | | | | | |
|---|---|---|---|---|---|---|---|---|
| | 14 | 15 | 16 | 17 | 18 | 19 | 20 | 21 |
| resin type | PC | PC | PC/ABS (90/10) | PC/ABS (90/10) | PC/ABS (90/10) | PC/ASA (90/10) | PC/SAN (90/10) | PC/PBT (90/10) |
| a phosphorus-containing organosilicon compound (% by mass) *1 | | | | | | | | |
| A (Example 1) | 5 | — | 0.5 | — | — | — | — | — |
| B (Example 2) | — | 5 | — | 0.5 | — | — | — | — |
| C (Example 3) | — | — | — | — | — | — | — | — |
| D (Examples 4 and 5) | — | — | — | — | 0.5 | 2 | 2 | 2 |
| other additives (% by mass) *1 | | | | | | | | |
| an antidripping agent | — | 0.5 | — | — | — | 0.5 | — | — |
| talc | — | — | — | 15 | 15 | 15 | 15 | 15 |
| glass fiber | 30 | 30 | — | — | — | — | — | — |

TABLE 2-continued

|  | Examples | | | | | | | |
|---|---|---|---|---|---|---|---|---|
|  | 14 | 15 | 16 | 17 | 18 | 19 | 20 | 21 |
| performance evaluation flame retardancy (rank) | | | | | | | | |
| initial state | V-0 | V-0 | V-0 | V-0 | V-0 | V-0 | V-0 | V-0 |
| after storage | V-0 | V-0 | V-0 | V-0 | V-0 | V-0 | V-0 | V-0 |
| appearance | ◉ | ◉ | ◉ | ◉ | ◉ | ◉ | ◉ | ◉ |
| flexural modulus ($10^3 \times$ Kg/cm$^2$) | 76 | 78 | 24 | 50 | 49 | 48 | 48 | 48 |
| impact strength (Kg · cm/cm) | 15 | 15 | 80 | 40 | 40 | 48 | 46 | 45 |
| heat distortion temperature (° C.) | 156 | 156 | 132 | 138 | 138 | 142 | 142 | 138 |

*1: based on total mass of a composition

TABLE 3

| Examples/Comparative Examples | Examples | | | | | Comparative Examples | |
|---|---|---|---|---|---|---|---|
|  | 22 | 23 | 24 | 25 | 26 | 4 | 5 |
| resin type | PBT | PET | PS | PC | PC | PC | PC |
| a phosphorus-containing organosilicon compound (% by mass) *1 | | | | | | | |
| A (Example 1) | — | — | — | — | — | — | — |
| B (Example 2) | — | — | — | 2 | — | — | — |
| C (Example 3) | — | — | — | — | — | — | — |
| D (Examples 4 and 5) | 2 | 2 | 3 | 3 | 10 | — | — |
| a phosphorus type additive (% by mass) *1 triphenylphosphate | — | — | — | — | 0.5 | — | 10 |
| silicon powder (% by mass) *1 | — | — | — | — | — | 20 | 10 |
| other additives (% by mass) *1 | | | | | | | |
| an antidripping agent | — | — | — | — | — | 0.5 | 0.5 |
| talc | — | — | — | — | — | — | — |
| glass fiber | — | — | — | — | — | — | — |
| performance evaluation flame retardancy (rank) | | | | | | | |
| initial state | V-0 | V-0 | V-0 | V-0 | V-0 | V-1 | V-1 |
| after storage | V-0 | V-0 | V-0 | V-0 | V-0 | V-1 | V-1 |
| appearance | ◉ | ◉ | ◉ | ◉ | ◉ | X | X |
| flexural modulus ($10^3 \times$ Kg/cm$^2$) | — | — | — | 24 | 22 | 18 | 19 |
| impact strength (Kg · cm/cm) | 50 | 50 | 23 | 80 | 84 | 16 | 18 |
| heat distortion temperature (° C.) | 62 | 75 | 98 | 134 | 136 | 63 | 60 |

*1: based on total mass of a composition

Trade names of resins and each component shown in Tables 1 to 3 are as follows:
Polycarbonate (PC) resin: "CALIBRE™ 300" from Sumitomo Dow Limited.
Acrylonitrile-butadiene-styrene (ABS) resin: "SANTAC® UT-61" from Mitsui Toatsu Chemicals Inc. and "Cevian V-680" from Daicel Chem. Ind. Ltd.
Polybutylene terephthalate (PBT) resin: "TUFPET" from Toyobo Co., Ltd. Acrylate-styrene-acrylonitrile (ASA), resin: "Dialak® A" from Mitsubishi Rayon Co., Ltd.
Styrene-acrylonitrile (SAN) resin: "Denka AS" from Denki kagaku Kogyo K.K.
Polyethylene terephthalate (PET) resin: "Dianite®" from Mitsubishi Rayon Co., Ltd.
Polystyrene (PS) resin: "Idemitsu polystyrene" from Idemitsu Petrochemical Co., Ltd.
Antidripping agent: "Polyflon F201L" from Daikin Ind. Ltd.
Silicone powder: "DC4-7051" from Dow corning.

As is clear from performance evaluation results shown in Tables 1 to 3, a molded part consisting of a resin composition containing a phosphorus-containing organosilicon compound of the present invention was superior in flame retardancy performance (initial state/after storage), appearance, flexural modulus, Izod impact strength and heat distortion temperature.

Example 27 and Comparative Example 6

(Preparation and Evaluation of Coating Compositions)

As Example 27, a coating composition was obtained by uniformly mixing 3.0 parts by mass of a phosphorus-containing organosilicon compound obtained in Example 2, 20 parts by mass of tetraethoxysilane and 45 parts by mass of isopropyl alcohol.

This coating composition was applied to a copper plate of 3×10 cm, followed by standing still in a room at 25° C. for 24 hours to obtain cured coating film. This film was set upright for 3 hours in a 100 L glass bottle containing 30 g of a 0.5% aqueous solution of hydrochloric acid. As a comparison (a blank) a copper plate without coating was simultaneously set upright for the same period in the above-described glass bottle.

The copper plate processed with a coating composition of the present invention showed no change at surface above the liquid level and kept initial color at surface below liquid level, although gloss was lost a little. On the other hand, the copper plate without coating turned dark red at surface above the liquid level and turned dark brown at surface below liquid level with complete loss of gloss.

As Comparative Example 6, a coating composition was obtained by uniformly mixing 3.0 parts by mass of methyltrimethoxysilane, 20 parts by mass of tetraethoxysilane and 45 parts by mass of isopropyl alcohol.

Similar evaluation as in Example 27 showed color change to dark red at surface above the liquid level and dark brown at surface below liquid level with complete loss of gloss just like a copper plate without coating.

As shown above, the present invention provides a new phosphorus-containing organosilicon compound, a method for producing the same and a resin composition or a coating composition containing the same. This phosphorus-containing organosilicon compound can exert the effects as molded parts such as fibers and films, coating agents and other processing agents because of having fire resistance, flame retardancy and antibiotic performance (in particular, antibiotic durability), along with consideration on safety and in particular, improving surface performance or resin performance by application to a resin. In particular, said compound has very superior characteristics as a flame retardant for various resins and can exert flame retardancy of 5 to 20 times conventionally known phosphorus type flame retardants when used in the same mass. Therefore, the addition amount to a resin can be reduced significantly, which can substantially prevent problems such as lowering of mechanical strength and heat distortion of resin compositions (molded parts) caused by the addition of a flame retardant.

What is claimed is:

1. A phosphorus-containing organosilicon compound, characterized by having in the molecule a phosphorus-containing group (an X group) bonded to a silicon atom and represented by the following chemical formula (6'):

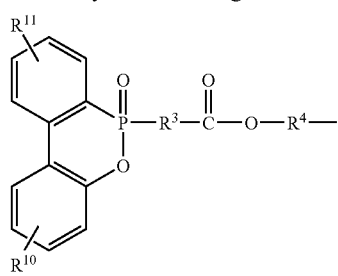

(6')

wherein $R^3$ and $R^4$ each independently represents a substituted or unsubstituted bivalent hydrocarbon group; and $R^{10}$ and $R^{11}$ may be the same or different each other and each represents a hydrogen atom, a halogen atom, an alkyl group having 1 to 4 carbon atoms or an alkoxy group having 1 to 4 carbon atoms.

2. A phosphorus-containing organosilicon compound, characterized by being represented by the following chemical formula (2):

$$X_a R^5_b SiO_{(4-a-b)/2} \quad (2)$$

[wherein X is a phosphorus-containing group represented by the chemical formula (6'):

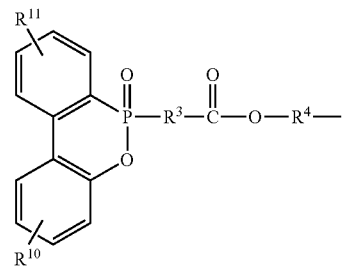

(6')

wherein $R^3$ and $R^4$ each independently represents a substituted or unsubstituted bivalent hydrocarbon group; and $R^{10}$ and $R^{11}$ may be the same or different each other and each represents a hydrogen atom, a halogen atom, an alkyl group having 1 to 4 carbon atoms or an alkoxy group having 1 to 4 carbon atoms.); $R^5$ represents the same or different an organic groups selected from an alkyl group, an aryl group, an aralkyl group, and a fluorine-substituted alkyl or alkoxy group each having 1 to 30 carbon atoms; a and b are numbers in the range of $0.001 \leq a \leq 1.5$ and $0 \leq b \leq 3.0$, respectively].

3. The phosphorus-containing organosilicon compound according to claim 2, wherein the chemical formula (2) is represented by the following chemical formula (3).

$$R^5_3 SiO-(R^5_2 SiO)x(R^5 XSiO)y-SiR^5_3 \quad (3)$$

(wherein, $R^5$ and X are each the same as the above; x is an integer of 0 or not less than 1; and y is an integer of not less than 1).

4. A phosphorus-containing organosilicon compound or a condensate thereof, characterized by being represented by the following chemical formula (4):

$$XSiR^6_c(OR^7)_{(3-c)} \quad (4)$$

[wherein X is a phosphorus-containing group represented by the chemical formula (6'):

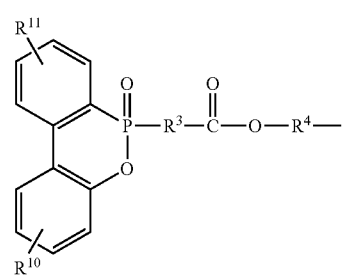

(6')

wherein $R^3$ and $R^4$ each independently represents a substituted or unsubstituted bivalent hydrocarbon group; and $R^{10}$ and $R^{11}$ may be the same or different each other and each represents a hydrogen atom, a halogen atom, an alkyl group having 1 to 4 carbon atoms or an alkoxy group having 1 to 4 carbon atoms.); $R^6$ is the same or different organic groups selected from an alkyl group, an aryl group, an aralkyl group, or a fluorine-substituted alkyl group each having 1 to 30 carbon atoms; $R^7$ represents the same or different organic groups selected from an alkyl group, an aryl group, an aralkyl group, or a fluorine-substituted alkyl group each having 1 to 30 carbon atoms; and c is 0 or 1].

5. A phosphorus-containing organosilicon compound, characterized by being represented by the following chemical formula (5):

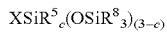 (5)

[wherein X is a phosphorus-containing group represented by the chemical formula (6'):

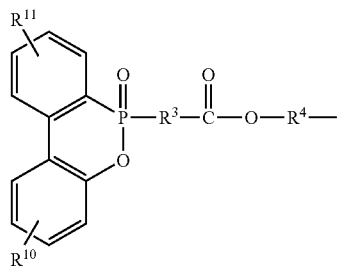

wherein $R^3$ and $R^4$ each independently represents a substituted or unsubstituted bivalent hydrocarbon group; and $R^{10}$ and $R^{11}$ may be the same or different each other and each represents a hydrogen atom, a halogen atom, an alkyl group having 1 to 4 carbon atoms or an alkoxy group having 1 to 4 carbon atoms.); $R^5$ is the same or different organic groups selected from an alkyl group, an aryl group, an aralkyl group, and a fluorine-substituted alkyl or alkoxy group each having 1 to 30 carbon atoms; $R^8$ represents the same or different organic groups selected from an alkyl group, an aryl group, an aralkyl group, and a fluorine-substituted alkyl or alkoxy group each having 1 to 30 carbon atoms; and c is 0 or 1].

6. A method for producing the phosphorus-containing organosilicon compound or the condensate thereof according to claim 1, characterized by that they are obtained by reaction of a compound represented by the following chemical formula (7):

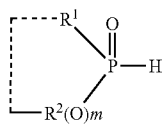 (7)

(wherein $R^1$ and $R^2$ may be the same or different, and each represents a linear or branched alkyl group having 1 to 8 carbon atoms, an alicyclic group having 5 to 6 carbon atoms in the ring, an unsubstituted or substituted aryl group having 6 to 10 carbon atoms, or a group forming a 5 to 8-membered ring with a phosphorus atom; and m is 0 or 1) and a silicon compound having in the molecule an unsaturated ester group bonded to a silicon atom, represented by the following chemical formula (8):

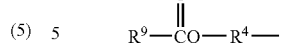 (8)

(wherein $R^4$ represents a substituted or unsubstituted bivalent hydrocarbon group; and $R^9$ represents a substituted or unsubstituted unsaturated hydrocarbon group).

7. A method for producing the phosphorus-containing organosilicon compound, or the condensate thereof according to claim 4, characterized by that they are obtained by reaction of a compound represented by the following chemical formula (7):

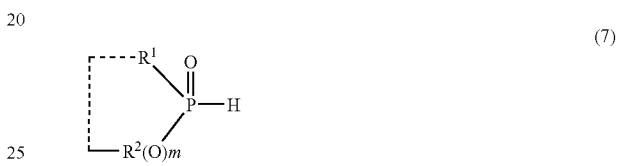 (7)

(wherein $R^1$ and $R^2$ may be the same or different, and each represents a linear or branched alkyl group having 1 to 8 carbon atoms, an alicyclic group having 5 to 6 carbon atoms in the ring, an unsubstituted or substituted aryl group having 6 to 10 carbon atoms, or a group forming a 5 to 8-membered ring with a phosphorus atom; and m is 0 or 1) and a silicon compound represented by the following chemical formula (9):

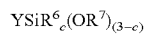 (9)

[wherein Y is an unsaturated ester group represented by the chemical formula (8):

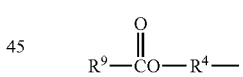 (8)

(wherein $R^4$ represents a substituted or unsubstituted bivalent hydrocarbon group; $R^9$ represents a substituted or unsubstituted unsaturated hydrocarbon group); $R^6$ represents the same or different organic groups selected from an alkyl group, an aryl group, an aralkyl group or a fluorine-substituted alkyl group each having 1 to 30 carbon atoms; $R^7$ represents the same or different organic groups selected from an alkyl group, an aryl group, an aralkyl group or a fluorine-substituted alkyl group each having 1 to 30 carbon atoms; and c is 0 or 1].

8. A method for producing the phosphorus-containing organosilicon compound, according to claim 1, characterized by that they are obtained using the phosphorus-containing organosilicon compound, or the condensate thereof as an intermediate, the phosphorus-containing organosilicon compound or a condensate thereof, being represented by the following chemical formula (4):

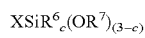 (4)

[wherein X is a phosphorus-containing group represented by the chemical formula (6'):

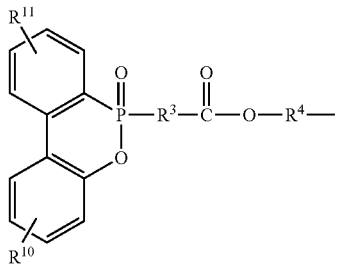
(6')

(wherein $R^3$ and $R^4$ each independently represents a substituted or unsubstituted bivalent hydrocarbon group; and $R^{10}$ and $R^{11}$ may be the same or different each other and each represents a hydrogen atom, a halogen atom, an alkyl group having 1 to 4 carbon atoms or an alkoxy group having 1 to 4 carbon atoms.); $R^6$ is the same or different organic groups selected from an alkyl group, an aryl group, an aralkyl group, or a fluorine-substituted alkyl group each having 1 to 30 carbon atoms; $R^7$ represents the same or different organic groups selected from an alkyl group, an aryl group, an aralkyl group, or a fluorine-substituted alkyl group each having 1 to 30 carbon atoms; and c is 0 or 1].

9. A resin composition, characterized by containing the phosphorus-containing organosilicon compound, or the condensate thereof according to claim 1.

10. The resin composition according to claim 9, characterized by being a polyester or polycarbonate resin composition.

11. A coating composition, characterized by containing the phosphorus-containing organosilicon compound, or the condensate thereof according to claim 1.

12. A method for producing the phosphorus-containing organosilicon compound or the condensate thereof according to claim 2, characterized by that they are obtained by reaction of a compound represented by the following chemical formula (7):

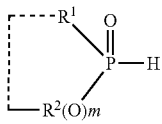
(7)

(wherein $R^1$ and $R^2$ may be the same or different, and each represents a linear or branched alkyl group having 1 to 8 carbon atoms, an alicyclic group having 5 to 6 carbon atoms in the ring, an unsubstituted or substituted aryl group having 6 to 10 carbon atoms, or a group forming a 5 to 8-membered ring with a phosphorus atom; and m is 0 or 1) and a silicon compound having in the molecule an unsaturated ester group bonded to a silicon atom, represented by the following chemical formula (8):

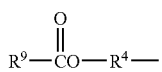
(8)

(wherein $R^4$ represents a substituted or unsubstituted bivalent hydrocarbon group; and $R^9$ represents a substituted or unsubstituted unsaturated hydrocarbon group).

13. A method for producing the phosphorus-containing organosilicon compound or the condensate thereof according to claim 4, characterized by that they are obtained by reaction of a compound represented by the following chemical formula (7):

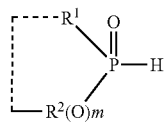
(7)

(wherein $R^1$ and $R^2$ may be the same or different, and each represents a linear or branched alkyl group having 1 to 8 carbon atoms, an alicyclic group having 5 to 6 carbon atoms in the ring, an unsubstituted or substituted aryl group having 6 to 10 carbon atoms, or a group forming a 5 to 8-membered ring with a phosphorus atom; and m is 0 or 1) and a silicon compound having in the molecule an unsaturated ester group bonded to a silicon atom, represented by the following chemical formula (8):

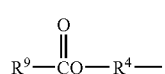
(8)

(wherein $R^4$ represents a substituted or unsubstituted bivalent hydrocarbon group; and $R^9$ represents a substituted or unsubstituted unsaturated hydrocarbon group).

14. A method for producing the phosphorus-containing organosilicon compound or the condensate thereof according to claim 5, characterized by that they are obtained by reaction of a compound represented by the following chemical formula (7):

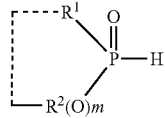
(7)

(wherein $R^1$ and $R^2$ may be the same or different, and each represents a linear or branched alkyl group having 1 to 8 carbon atoms, an alicyclic group having 5 to 6 carbon atoms in the ring, an unsubstituted or substituted aryl group having 6 to 10 carbon atoms, or a group forming a 5 to 8-membered ring with a phosphorus atom; and m is 0 or 1) and a silicon compound having in the molecule an unsaturated ester group bonded to a silicon atom, represented by the following chemical formula (8):

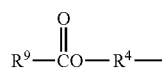
(8)

(wherein $R^4$ represents a substituted or unsubstituted bivalent hydrocarbon group; and $R^9$ represents a substituted or unsubstituted unsaturated hydrocarbon group).

15. A method for producing the phosphorus-containing organosilicon compound, according to claim 2, characterized by that they are obtained using the phosphorus-containing organosilicon compound, or the condensate thereof as an intermediate, the phosphorus-containing organosilicon compound or a condensate thereof, being represented by the following chemical formula (4):

$$XSiR^6_c(OR^7)_{(3-c)} \tag{4}$$

[wherein X is a phosphorus-containing group represented by the chemical formula (6'):

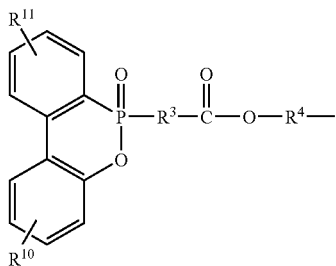

(6')

(wherein $R^3$ and $R^4$ each independently represents a substituted or unsubstituted bivalent hydrocarbon group; and $R^{10}$ and $R^{11}$ may be the same or different each other and each represents a hydrogen atom, a halogen atom, an alkyl group having 1 to 4 carbon atoms or an alkoxy group having 1 to 4 carbon atoms.); $R^6$ is the same or different organic groups selected from an alkyl group, an aryl group, an aralkyl group, or a fluorine-substituted alkyl group each having 1 to 30 carbon atoms; $R^7$ represents the same or different organic groups selected from an alkyl group, an aryl group, an aralkyl group, or a fluorine-substituted alkyl group each having 1 to 30 carbon atoms; and c is 0 or 1].

16. A method for producing the phosphorus-containing organosilicon compound, according to claim 5, characterized by that they are obtained using the phosphorus-containing organosilicon compound, or the condensate thereof as an intermediate, being represented by the following chemical formula (4):

$$XSiR^6_c(OR^7)_{(3-c)} \tag{4}$$

[wherein X is a phosphorus-containing group represented by the chemical formula (6'):

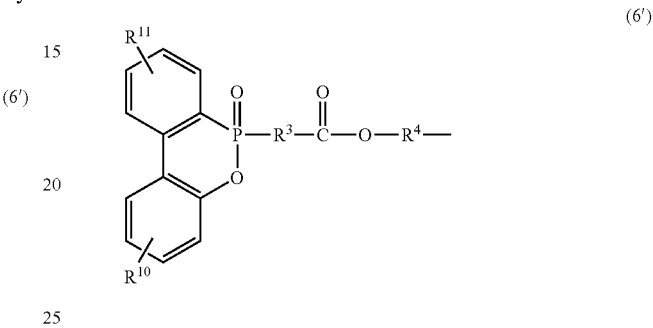

(6')

(wherein $R^3$ and $R^4$ each independently represents a substituted or unsubstituted bivalent hydrocarbon group; and $R^{10}$ and $R^{11}$ may be the same or different each other and each represents a hydrogen atom, a halogen atom, an alkyl group having 1 to 4 carbon atoms or an alkoxy group having 1 to 4 carbon atoms.); $R^6$ is the same or different organic groups selected from an alkyl group, an aryl group, an aralkyl group, or a fluorine-substituted alkyl group each having 1 to 30 carbon atoms; $R^7$ represents the same or different organic groups selected from an alkyl group, an aryl group, an aralkyl group, or a fluorine-substituted alkyl group each having 1 to 30 carbon atoms; and c is 0 or 1].

* * * * *